United States Patent [19]

Yamada et al.

[11] Patent Number: 4,680,263

[45] Date of Patent: Jul. 14, 1987

[54] CONTINUOUS ALCOHOL MANUFACTURING PROCESS USING IMMOBILIZED MICROORGANISM

[75] Inventors: Tomiaki Yamada, Yokohama; Masuo Kamihonoki, Ishioka; Hiroshi Sagara; Hiroshi Umino, both of Yokohama, all of Japan

[73] Assignees: New Energy Development Organization; JGC Corporation; Sanraku-Ocean Co., Ltd., all of Tokyo, Japan

[21] Appl. No.: 534,530

[22] Filed: Sep. 22, 1983

[30] Foreign Application Priority Data

Sep. 27, 1982 [JP] Japan ................................ 57-169349

[51] Int. Cl.$^4$ .......................... C12P 7/14; C12P 7/06; C12M 1/40
[52] U.S. Cl. ..................................... 435/162; 435/161; 435/288; 435/813; 435/819
[58] Field of Search .............................. 435/161–165, 435/288, 174, 813, 819

[56] References Cited

U.S. PATENT DOCUMENTS

| | | | |
|---|---|---|---|
| 4,349,628 | 9/1982 | English et al. | 435/165 X |
| 4,376,163 | 3/1983 | Ehnström | 435/165 X |
| 4,385,118 | 5/1983 | Muller et al. | 435/813 X |
| 4,403,034 | 9/1983 | Rogers et al. | 435/165 X |
| 4,460,687 | 7/1984 | Ehnström | 435/813 X |
| 4,522,920 | 6/1985 | Thorsson et al. | 435/161 |
| 4,546,081 | 10/1985 | Yamada et al. | 435/161 |

OTHER PUBLICATIONS

Mattiasson, Immobilized Cells and Organelles, vol. 1, CRC Press, Boca Raton, 1983, pp. 122–128.
Pitcher, Jr., Immobilized Enzymes for Food Processing, CRC Press, Boca Raton, 1980, pp. 158–163.

*Primary Examiner*—Esther M. Kepplinger
*Assistant Examiner*—Shawn P. Foley
*Attorney, Agent, or Firm*—Flynn, Thiel, Boutell & Tanis

[57] ABSTRACT

A feed liquid (sugar-containing liquid) is continuously fed to a fermenter packed with an immobilized microorganism, which is obtained by immobilizing an alcohol producing microorganism on a carrier, for alcohol fermentation. The fermentation liquid is continuously taken out of said fermenter and is heated to a temperature of 35° to 80° C. This liquid is introduced into a flash tank maintained at reduced pressure and is divided into an alcohol-containing steam and a liquid. The alcohol-containing steam is condensed and recovered as alcohol, while the separated liquid is cooled and is cycled back to said fermenter.

26 Claims, 2 Drawing Figures

CONTINUOUS ALCOHOL MANUFACTURING PROCESS USING IMMOBILIZED MICROORGANISM

BACKGROUND OF THE INVENTION (a) Field of the invention

The present invention relates to a process for continuously manufacturing alcohol from a sugar-containing liquid by using an immobilized microorganism which is obtained by immobilizing an alcohol producing microorganism on a carrier.

(b) Description of the prior art

Alcohol (ethanol) has hitherto been manufactured by the fermentation method and has been used for such wide purposes as drinks, medicines, toiletries and the like. Additionally, people have begun to entertain some apprehension about the exhaustion of fossil fuels, in particular, petroleum. Various studies have been carried out for the purpose of utilizing alcohol as an alternate energy source for petroleum. Therefore, the demand for establishment of an alcohol fermentation method which can meet the requirements for high alcohol productivity and energy conservation has increased.

The fermentation method which can satisfy these requirements should enhance the volumetric efficiency of the fermenter (alcohol productivity per unit volume of the fermenter and unit time) and simultaneously reduce energy consumption taking into consideration not only the fermentation step but also the alcohol-separating step and the waste liquid-treating step. However, such an efficient and economical alcohol fermentation method has not been proposed yet.

In alcohol fermentation, although there are some differences between the microorganisms to be employed, it may be generally stated that as the alcohol concentration in the fermenter increases fermentation speed is largely decreased by the presence of alcohol and other metabolic products of the fermentation process. For instance, when using an alcohol producing yeast, a serious hindrance to the fermentation speed is detectable when the alcohol concentration reaches approximately 7 to 8 wt.% or more, thereby decreasing alcohol formation. In view of this, it was inevitable that conventional methods carry out fermentation in a low alcohol concentration solution. Such a method brings about the problem of treating a large amount of fermentation waste liquid and the necessity of recovering the alcohol from the low alcohol concentration solution. Accordingly, this method is defective because considerably large amounts of energy must be consumed in solving those problems.

As the means for solving those problems of the above-described process, there has been proposed a method which comprises treating the fermentation liquid taken out of the fermenter under reduced pressure to thereby separate the alcohol from the liquid. For instance, Japanese Laid Open Patent Application No. 21592/1981 and Japanese Laid Open Patent Application No. 2685/1982 disclose methods wherein the fermentation liquid taken out of the fermenter is continuously divided into alcohol-containing steam and yeast liquid at a temperature which exerts no influence on the yeast allowing under reduced pressure, and the yeast liquid to be cycled back to the fermenter. These methods are intended to reduce the treatment of the residual fermentation liquid discharged out of the system and to utilize the yeast liquid again in the fermenter.

In removing the alcohol from the fermentation liquid and returning the yeast liquid to the fermenter for reuse, it is necessary that the temperature of the fermentation liquid introduced into the reduced pressure system be lower than the temperature which exerts an influence upon the yeast. In order that the alcohol fermentation may be effected according to this method it is necessary, because the alcohol concentration in the fermenter is low, to further reduce the pressure in the separation step or increase the amount of the yeast liquid which is cycled. Therefore, this method is unavoidably followed by an increase in energy consumed in maintaining the reduced pressure state or in cycling the liquid, and should not be said to be economical.

Japanese Laid Open Patent Application No. 64790/1981 has proposed a method which comprises taking the yeast-containing fermentation liquid out of the fermenter, dividing this liquid into an enriched yeast flow and a yeast-free flow by means of a centrifugal separator or the like, cycling the enriched yeast flow to the fermenter, heating the yeast-free flow to a desired temperature and then introducing it to the evaporation unit device under reduced pressure. However, this method is not always preferable is that not only is the construction of such a unit complicated, but also the cost of equipment, is high particularly for a centrifugal separator capable of treating a large amount of the fermentation liquid, and further, the operating costs are very expensive.

SUMMARY OF THE INVENTION

The object of the present invention is to provide a continuous alcohol fermentation process which is capable of eliminating the aforesaid problems or defects inherent in the conventional methods as well as providing a fermentation process of high productivity (a high volumetric efficiency of the fermenter).

The continuous alcohol manufacturing process according to the present invention is characterized in that a fermenter is packed with an immobilized microorganism which is obtained by immobilizing an alcohol producing microorganism on a carrier; a sugar-containing liquid is continuously supplied to said fermenter so as to effect alcohol fermentation; part of said fermentation liquid is continuously taken out of the fermenter and heated to 35° to 80° C.; this is introduced into a flash tank held under reduced pressure thereby to divide it into an alcohol-containing steam and a liquid; said alcohol-containing steam is condensed for recovery; and at least part of said separated liquid is cooled and cycled to the fermenter.

DETAILED DESCRIPTION OF THE PREFERRED EMBODIMENTS

The process according to the present invention will be explained in more detail hereinafter. According to the process of the present invention, it is envisioned that the alcohol-containing steam be fully separated from the fermentation liquid without lowering the pressure within the flash tank too much, by (i) using the alcohol producing microorganism immobilized on a carrier, namely as the so-called immobilized microorganism and (ii) heating the fermentation liquid taken out of the fermenter to a relatively high temperature (35° to 80° C., preferably 40° to 80° C.).

As the microorganism used in the process of the present invention there can be generally enumerated yeasts selected from Saccharomyces genus, Zygosaccharomyces genus and Schizosaccharomyces genus, and bacterium such as Zymomonas genus and the like. Regarding the immobilization of the microorganisms, there is no one particular way in which this should be accomplished, but it is desirable that the microorganisms be immobilized so that they may grow. Microbes, which keep living and growing in the immobilized state, may also be called immobilized growing cells and immobilized living cells. It is preferable that the carriers be covered with immobilized microorganisms. Such carriers include, for instance, natural high molecular compounds such as agar, alginate, k-carrageenan, gelatin, collagen and the like, and high molecular compounds resulting from polymerization of monomers such as polyacrylamide, photocrosslinked resins and the like.

Generally speaking, the immobilized microorganism and the manufacturing process thereof are well known.

The carrier covered with the immobilized microorganism is formed into a suitable size and a suitable shape, and charged into the fermenter. As the form of the fermenter there may be employed any one of the normal forms, such as packed bed, suspension bed, moving bed and the like.

Figure 1:
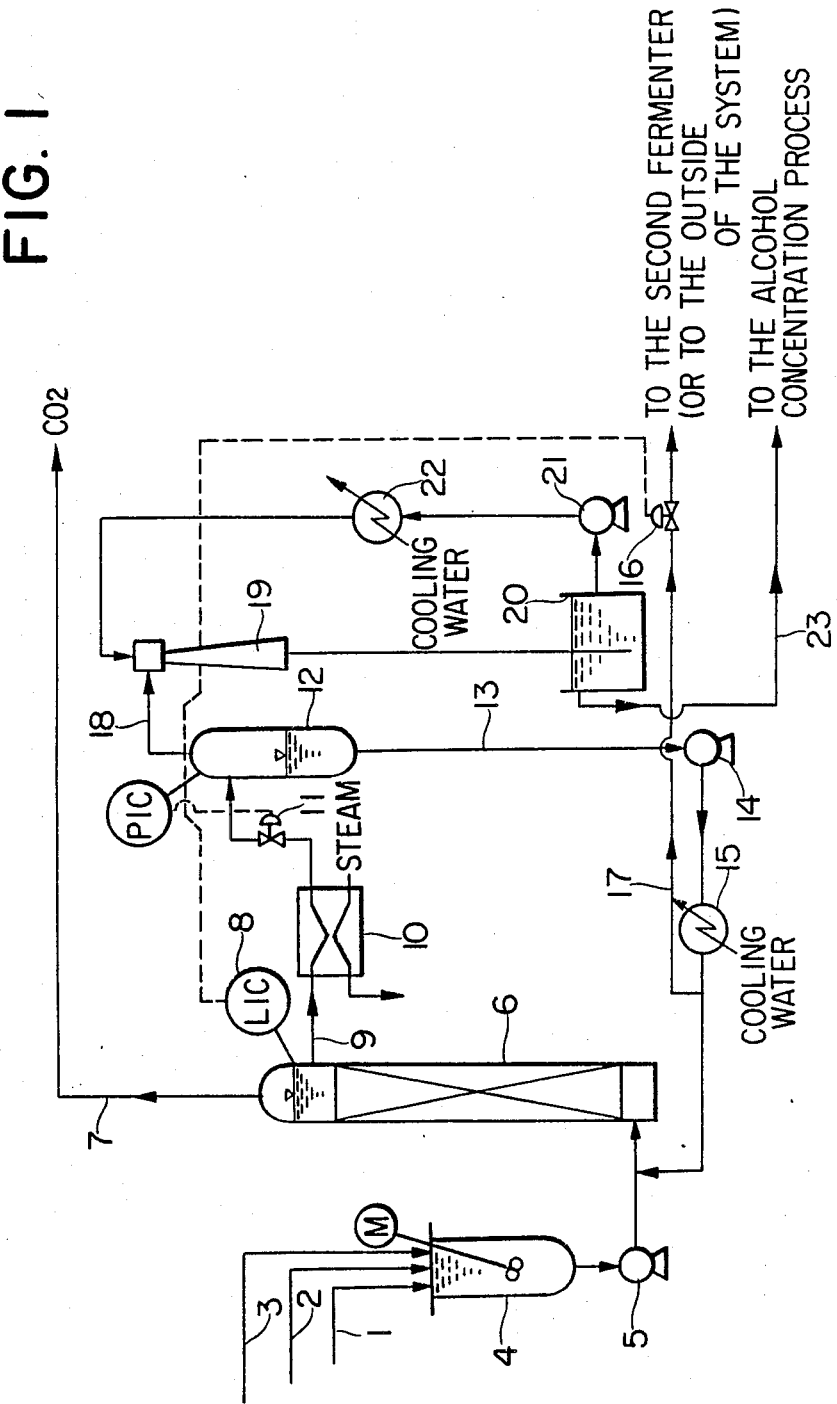
FIG. 1 is a flow diagram of a first embodiment of the invention.

Of the accompanying drawings, FIG. 1 is a schematic view showing the general arrangement of the first fermenter (or the general arrangement of the fermenter in case there is only one fermenter). The process according to the present invention will be explained based on FIG. 1 as follows.

A sugar-containing liquid is introduced through line 1, a secondary feed is introduced through line 2 and water is introduced through line 3, respectively, in a feed preparation tank 4, and a predetermined concentration of sugar-containing liquid is prepared. The sugar concentration of the feed liquid (sugar-containing liquid) is determined according to the concentration of the final alcohol to be obtained, but is normally about 10 to 250 g/l. In case the process of the present invention is directed toward high concentration alcohol fermentation, it is desirable that the sugar concentration of the feed liquid be about 250 to 400 g/l.

The sugar-containing liquid is introduced in a first fermenter 6 through a feed supply pump 5. The first fermenter 6 is charged with alcohol producing microorganisms immobilized on carriers wherein the immobilized microorganisms contact the feed liquid and thereby produce alcohol. The temperature in the first fermenter 6, which also has a bearing on the fermentation characteristics of the microorganisms, is normally maintained at 25° to 35° C. in the case of yeast. Referred to afterwards, this temperature is maintained by cycling part of the liquid, which is taken out of a flash tank and cooled, to the first fermenter 6. The fermentation pressure within the first fermenter 6 is preferable to be normal pressure or somewhat positive pressure (normal pressure to 2 Kg/cm²G). Although not shown herein, it is intended that a proper amount of air or oxygen is introduced in the first fermenter 6.

In the first fermenter 6, carbon dioxide is produced simultaneously with alcohol, said carbon dioxide being discharged to the outside of the system through line 7. The level of the upper liquid surface of the first fermenter 6 is controlled by means of a liquid level controller (LIC) 8, and part of the fermentation liquid is designed to flow out of the fermenter continuously through line 9.

The fermentation liquid, which has flowed out through line 9, is heated to a desirable temperature (35° to 80° C., preferably 40° to 80° C.) by means of a heater 10, and then is introduced into a flash tank 12 maintained under reduced pressure by means of a pressure regulating valve 11.

In the flash tank 12, the alcohol and water contained in the fermentation liquid are evaporated in the form of alcohol-containing steam, and the separated liquid passes through line 13, is fed to a cooler 15 through a circulating pump 14, and then is cycled to a first fermenter 6.

Part of the liquid cooled here is introduced into a second fermenter from line 17 through a liquid level controlling valve 16 which operates in cooperation with the liquid level controller 8. In this case, it is also possible that part of said separated liquid is introduced in the second fermenter from line 13 to line 17 (without cooling) and the balance is cooled by means of the cooler 15 and thereafter cycled to the first fermenter 6. In case alcohol is produced using a single fermenter, it follows that the liquid flowing through line 17 is discharged out of the system.

It is possible to choose the pressure within the flash tank 12 and the amount of the liquid, which has been separated in the flash tank 12, to be cycled to the first fermenter 6 as the occasion may demand, taking into consideration the alcohol-containing steam intended to obtain and the relation of the established temperature of the fermentation liquid. Normally, it is preferred that the pressure within the flash tank 12 be about 30 to 300 mmHg abs, and the amount of the separated liquid cycled to the first fermenter 6 be about 1 to 10 times as much as the amount of the feed liquid supplied to the first fermenter 6.

The alcohol-containing steam taken out of the flash tank 12 through line 18 is such by an ejector 19, and stored in water tank 20 for use in the ejector in the form of an alcohol-containing water. This alcohol-containing water in the water tank 20 for use in the ejector is cooled to a fixed temperature (25° to 35° C.) through a cooler 22 by means of a pump 21, thereafter utilized as the water for driving the ejector, and part of said water is taken out of the system through line 23 and fed to the alcohol concentration step. As the way of maintaining the pressure within the flash tank 12 at reduced pressure there is cited herein the instance of utilizing the ejector 19 for that purpose. However, another way may be to use a vacuum pump.

In the aforesaid explanation based on FIG. 1, for convenience' sake, the alcohol manufacturing process relating to the first fermenter 6 has been shown. It is to be noted that in the practice of the process of the present invention, the number (n) of fermenters used may be single or plural, and especially when alcohol fermentation is effected continuously by arranging the fermenters in series (namely, arranging the process as illustrated in FIG. 1 in plural and in series) the excellent results can be achieved. In this instance, the sufficient number (n) of fermenters used is 2 to 5.

Figure 2:
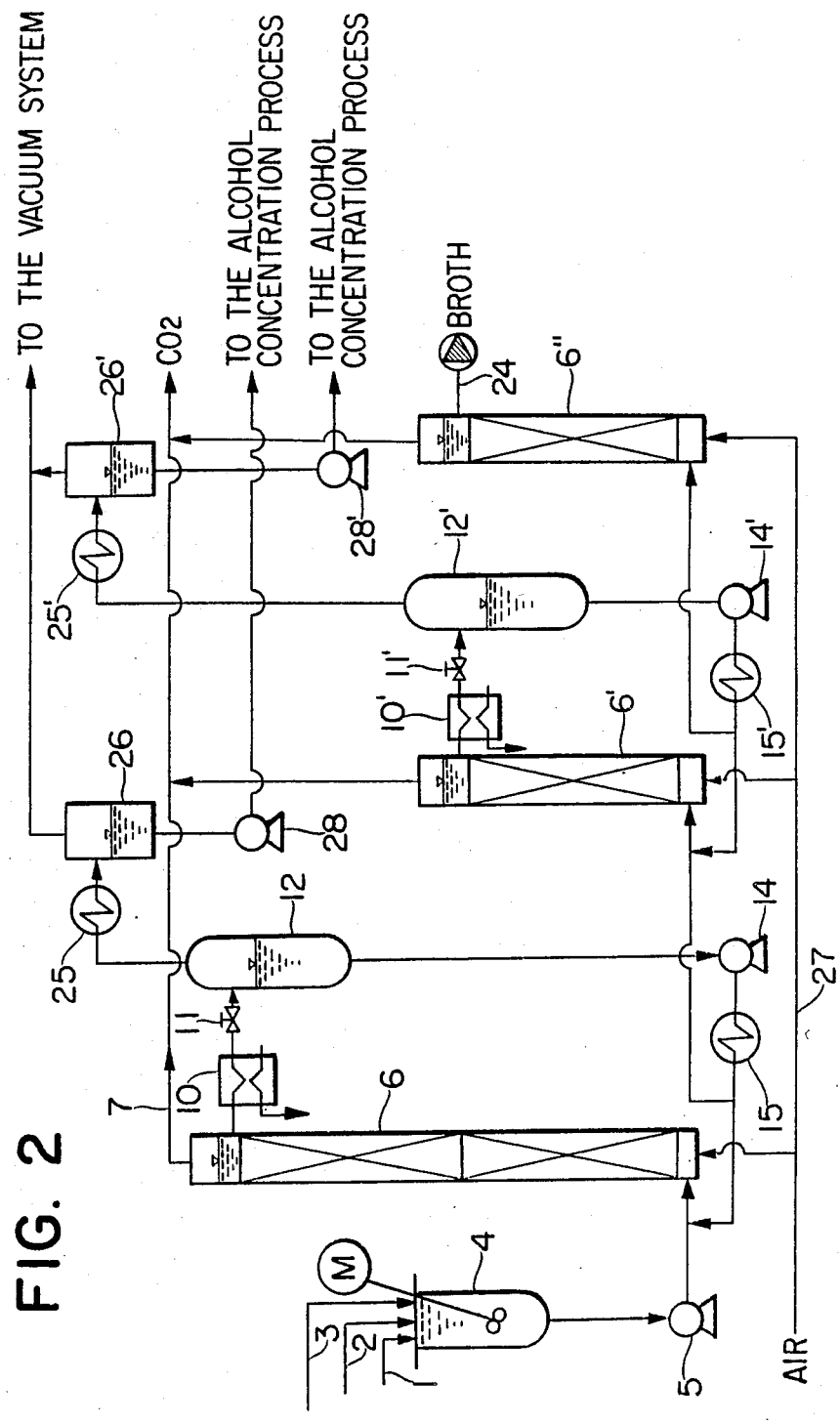
FIG. 2 is a flow diagram of a second embodiment of the invention.

FIG. 2 shows schematically three fermenters are arranged in series and how continuous alcohol fermentation is effected, wherein the same operation as a first fermenter 6 is conducted by a second fermenter 6' and a third fermenter 6''. The sugar in the feed liquid is almost consumed in the final fermenter (the third fermenter 6'' in this case), the fermented liquid (broth) is discharged through line 24 and thus a series alcohol fermentation operation is completed. In FIG. 2, reference numeral 11' denotes a pressure regulating valve and 27 denotes an air inlet line.

As described above, the present invention effects alcohol fermentation by using the immobilized microorganisms (obtained by immobilizing alcohol producing microorganisms on a carrier). Accordingly, the fermentation liquid taken out of the fermenter scarcely contains any of the microorganism and, if contained, re-use of said microorganism for alcohol fermenting purpose is not intended. Therefore, when said fermentation liquid is introduced in the flash tank maintained at reduced pressure, there is no need to consider the influence of the heating temperature of said fermentation liquid especially upon the microorganism mass, whereby it becomes possible to hold the fermentation liquid at a relatively high temperature. Accordingly, in the present invention, the alcohol-containing steam can be sufficiently separated from the fermentation liquid without lowering the pressure within the flash tank greatly and/or greatly increasing the amount of the liquid separated from the flash tank and cycled to the fermenter, whereby it becomes easy to hold the alcohol concentration in the fermenter at a sufficiently low degree and permits the continuous alcohol fermentation process resulting in high alcohol productivity.

EXAMPLES

EXAMPLE 1

Urethanated prepolymer (average molecular weight: about 5000) comprising 2000 g of polyethylene glycol (molecular weight: about 4000), 1 mol (222 g) of isophoronediisocyanate and 1 mol (130 g) of 2-hydroxyethyl methacrylate was admixed with 500 ml (60 g in terms of dry yeast) of *Saccharomyces formosensis* suspension and further with 2 g of benzoin ethylether as the photosensitizer. Then, the resulting mixture was dispersed uniformly by means of a homogenizer to thereby obtain a mixed liquid of yeast and prepolymer. In succession, a glass plate was covered with a polypropylene film (about 50$\mu$ in thickness). The circumference of the glass plate was surrounded with a spacer (about 1.0 mm in thickness), thereafter said mixed liquid of yeast and prepolymer was poured thereon, and its upper part was covered with the same polypropylene film to shut off air. The same was irradiated from below for about 3 minutes by means of a low pressure mercury lamp (main wavelength: 3600 Å), and then was turned upside down and irradiated likewise for about 3 minutes to thereby prepare a film-like immobilized yeast (thickness: about 1.08 mm).

The thus prepared plural pieces of immobilized yeast were cut to obtain (a) 40 long pieces of strip yeast (1.08 mm in thickness, 30 mm in width and 500 mm in length) and (b) 40 long pieces of strip yeast (1.08 mm in thickness, 30 mm in width and 350 mm in length). This immobilized yeast in the dry state was found to have a yeast concentration of 2.5 wt.% relative to the total weight.

In succession, 10 pieces of said (a) immobilized yeast were placed in a vessel (30 mm square in inside diameter and 500 mm in height) at regular intervals through a spacer. Four vessels, charged thus with the immobilized yeast, were piled perpendicularly to thereby prepare a square shaped fermenter (30 mm square in inside diameter and 2000 mm in total length). This is named a first fermenter. In this connection, it is to be noted that the total volume of the first fermenter is 1.8 l and 0.648 l of the immobilized yeast is received therein (36% in packing fraction).

10 pieces of said (b) immobilized yeast were placed in a vessel (30 mm square in inside diameter and 250 mm in height) at regular intervals through a spacer. The thus charged vessels were piled perpendicularly to prepare a second fermenter (30 mm square in inside diameter, 700 mm in total length and 0.63 l in total volume). A third fermenter was prepared in the same manner as the second fermenter.

Next, an experimental device for continuous alcohol fermentation as shown in FIG. 2 was prepared by the use of these three fermenters. The following tests were made using this device.

The feed molasses was diluted with water in the feed preparation tank 4. Ammonium sulfate was added thereto to prepare a feed liquid (sugar-containing liquid). Thereafter, the feed liquid was introduced in the first fermenter 6 by means of the pump 5 and a very small amount of additional air was supplied thereto for alcohol fermentation. The carbonic acid gas generated in the first fermenter 6 was discharged from the system through line 7 from the upper part of the fermenter.

The fermentation liquid flowing out of the upper part of the first fermenter 6 is heated indirectly with steam by means of the heater 10, then is passed through the pressure regulating valve 11 and is introduced to the first flash tank 12 maintained under reduced pressure (60 mmHg abs) by using a vacuum pump (not shown). The alcohol and water generated in the first flash tank 12 were turned into steam. This steam was dispersed from the upper part, was cooled and condensed with cooling water by means of a first cooler 25. This condensate was separated from noncondensed gas by means of a first liquid-vapor separator 26. The resulting condensate was transferred to a storage tank (not shown) disposed outside of the system by means of a pump 28 so as to measure the concentration and yield of the alcohol contained in the condensate.

On the other hand, the liquid flowing from the lower part of the first flash tank 12 was cooled to about 30° C. by the cooler 15 and thereafter a desired amount of it was cycled to the first fermenter 6 by means of the pump 14. The remainder thereof was transferred to the second fermenter 6' so that the upper liquid surface of the first fermenter 6 might be substantially constant.

The liquid introduced into the second fermenter 6' (this liquid still contains some substrate and is usable as either feed liquid or fermentation liquid) could also effect alcohol fermentation in the second fermenter as in the first fermenter.

Part of the fermentation liquid was taken out of the second fermenter 6', was heated by means of a heater 10', and thereafter was introduced into a second flash tank 12' maintained at reduced pressure (60 mmHg abs). The alcohol-containing steam dispersed from the upper part of a second flash tank 12' was introduced from a second cooler 25' to a second liquid-vapor separator 26'. The condensate obtained therein was transferred to a storage tank (not shown) disposed outside of the system by means of a pump 28' so as to measure the concentration and yield of the alcohol.

The liquid flowing from the lower part of the second flash tank 12' was, likewise in the case of the liquid flowing out of the lower part of said first flash tank 12, cooled and thereafter a desired amount thereof was cycled to the second fermenter 6' and the remainder thereof was transferred to a third fermenter 6".

The third fermenter 6" was made to function, in this experiment, mainly as a maturing tank which brings fermentation to completion. Therefore, the fermentation in this instance was a usual fermentation which was carried out at normal pressure and did not incorporate therein the reduced pressure flash circulating system as employed in the first and second fermenters, and the final product was taken out of the system as broth.

In case the above mentioned operations had been continued for a long period of time, it was found that both the amount of product alcohol and the amount of the condensate were somewhat variable for the initial 1 to 2 days, but after that time both the product alcohol and condensate showed a substantially definite composition. This phenomenon may be understood in that the variation observed for the initial 1 to 2 days is caused by growth of immobilized yeasts at the beginning of fermentation, and stability is reached at the time when the growth becomes substantially steady. The obtained test results are summarized in Table-1.

COMPARATIVE EXAMPLE 1

The test was carried out according to the exact same procedure as Example 1 except that the flash tanks 12 and 12' were held at normal pressures. The obtained results are summarized in Table-1.

EXAMPLE 2

Tests were carried out using the same apparatus as Example 1 and by variously changing the temperatures of the fermentation liquid heated by heaters 10 and 10', the pressure within the flash tanks 12 and 12' and the ratios of the cycled liquid amounts (amounts of liquids which are separated in the flash tanks 12 and 12' and cycled to the fermenters 6 and 6' respectively) to the feed supply amount.

These test results were summarized in Table-2, paying attention to the alcohol productivity and the alcohol product velocity, namely the volumetric efficiency in the first fermenter 6.

COMPARATIVE EXAMPLE 2

By using the same apparatus as Example 1, the test was carried out under the condition of not elevating the temperature of the fermentation liquid by means of heaters 10 and 10', namely under the condition of introducing fermentation liquid to the flash tanks 12 and 12' (pressure: 40 mmHg) at the normal fermentation temperature of 30° C. The thus obtained results were shown in Table-2 for the purpose of comparison with Example 2.

It can be clearly seen from the comparison with Example 2 that since the conventional method (Comparative Example 2) must restrict the inlet temperature of the flash tank to be lower than the temperature condition which does not affect the yeast, there is the necessity of severely restricting both the reduced pressure condition of the flash tank and the amount of the liquid cycled thereto.

TABLE 1

|  | Example 1 | | | Comparative Example 1 | | |
| --- | --- | --- | --- | --- | --- | --- |
|  | 1st fermenter | 2nd fermenter | 3rd fermenter | 1st fermenter | 2nd fermenter | 3rd fermenter |
| Amount of fermentative sugar in feed liquid or fermentation liquid (g/hr) | 159 | 51.7 | 17.9 | 159 | 80.5 | 57.8 |
| Feed speed of feed liquid or fermentation liquid (g/hr) | 674 | 517 | 465 | 674 | 637 | 620 |
| Temperature within fermenter (°C.) | 30 | 30 | 30 | 30 | 30 | 30 |
| Amount of cycled liquid feed amount of feed liquid or fermentation liquid | 3.0 | 3.0 | 0 | 0 | 0 | 0 |
| Temperature of fermentation liquid after heating (°C.) | 60 | 60 | — | — | — | — |
| Concentration of ethanol within fermenter (g/l) | 29.0 | 36.0 | 60.0 | 60.5 | 76.9 | 89.5 |
| Total evaporation amount (g/hr) | 107.0 | 35.8 | 0 | 0 | 0 | 0 |
| Amount of ethanol in evaporation gas (g/hr) | 37.0 | 12.7 | 0 | 0 | 0 | 0 |
| Ethanol concentration in evaporation gas or condensate (wt. %) | 34.6 | 35.5 | — | — | — | — |
| Amount of ethanol fed in the following fermenter or storage tank (g/hr) | 15.0 | 18.7 | 27.4 | 38 | 49 | 56 |
| Amount of ethanol generated in the proper fermenter (g/hr) | 52.0 | 16.4 | 8.7 | 38 | 11 | 7 |
| Volumetric efficiency of the proper fermenter (g-ethanol/l-fermenter · hr) | 28.9 | 26.0 | 13.8 | 21.1 | 17.5 | 11.1 |
| Amount of residual sugar *1 (g/hr) | 51.7 | 17.9 | 0 | 80.5 | 57.8 | 43.4 |
| Fermentation percentage (against the brewing fermentative sugar standard) (%) | — | — | 95.9 | — | — | 69.0 |
| Volumetric efficiency of the fermenter as a whole (g-ethanol/l-fermenter · hr) |  | 25.2 |  |  | 18.3 |  |

*1 fermenative sugar standard

TABLE 2

|  | Test Example 1 | 2 | 3 | 4 | 5 | 6 | 7 | 8 | 9 | 10 | 11 | 12 | 13 | 14 | Comparative Example 2 |
|---|---|---|---|---|---|---|---|---|---|---|---|---|---|---|---|
| Amount of circulating liquid/Amount of feed liquid | 1.0 | 1.0 | 1.0 | 1.0 | 1.0 | 1.0 | 1.0 | 3.0 | 3.0 | 3.0 | 3.0 | 3.0 | 3.0 | 3.0 | 30.0 |
| Temperature of fermentation liquid after heating (°C.) | 50 | 60 | 80 | 60 | 80 | 60 | 80 | 50 | 60 | 80 | 60 | 80 | 60 | 80 | 30 |
| Pressure of flash tank (mmHg) | 60 | 60 | 60 | 100 | 100 | 200 | 200 | 60 | 60 | 60 | 100 | 100 | 200 | 200 | 40 |
| Temperature of circulating liquid (°C.) | 30 | 30 | 30 | 30 | 30 | 30 | 30 | 30 | 30 | 30 | 30 | 30 | 30 | 30 | 30 |
| Total evaporation amount (g/hr) | 36.1 | 55.5 | 102.8 | 34.5 | 83.1 | 3.1 | 45.6 | 64.1 | 107.0 | 120.3 | 0.5 | 127.2 | 6.0 | 98.5 | 31.5 |
| Amount of ethanol in evaporation gas (g/hr) | 16.0 | 23.3 | 37.0 | 15.5 | 32.0 | 1.6 | 20.0 | 25.9 | 37.0 | 41.5 | 2.8 | 42.6 | 3.0 | 33.5 | 15.4 |
| Concentration of ethanol in evaporation gas (wt. %) | 44.0 | 41.9 | 36.0 | 44.9 | 38.5 | 51.6 | 43.9 | 40.4 | 34.6 | 34.5 | 56.0 | 33.5 | 50.0 | 34.0 | 49.0 |
| Concentration of ethanol in fermenter (wt. %) | 4.7 | 4.1 | 2.9 | 4.8 | 3.4 | 5.8 | 4.5 | 3.9 | 2.9 | 2.5 | 6.1 | 2.4 | 5.9 | 3.3 | 4.8 |
| Amount of ethanol fed to 2nd fermenter (g/hr) | 28.0 | 23.6 | 15.0 | 28.0 | 17.5 | 37.4 | 25.6 | 21.6 | 15.0 | 12.5 | 37.6 | 11.9 | 36.0 | 17.1 | 26.8 |
| Amount of ethanol generated in 1st fermenter (g/hr) | 44.0 | 47.0 | 52.0 | 43.5 | 49.5 | 39.0 | 45.6 | 47.5 | 52.0 | 54.0 | 37.9 | 54.5 | 39.0 | 50.6 | 42.2 |
| Fermenter volumetric efficiency (g-ethanol l-fermenter · hr) | 24.8 | 26.5 | 29.3 | 24.5 | 27.9 | 21.9 | 25.7 | 26.7 | 28.9 | 30.4 | 21.3 | 30.7 | 21.9 | 28.5 | 23.8 |

What is claimed is:

1. A continuous alcohol manufacturing process wherein, in a fermentation system, a fermenter is packed with an alcohol-producing microorganism immobilized on a carrier; comprising the steps of continuously supplying a sugar-containing liquid to said fermenter so as to effect alcohol fermentation; continuously removing from the fermenter a portion of said fermentation liquid which has contacted said immobilized microorganism; heating said removed liquid to a temperature of from 50° to 80° C. in a heater; introducing said heated liquid into a flash tank held under reduced pressure of from 60 to 300 mm Hg absolute thereby to divide said heated liquid into an alcohol-containing vapor and a separated liquid; condensing said alcohol-containing vapor and removing it from the fermentation system; cooling said separated liquid to a temperature equal to or below the temperature within the fermenter; continuously recycling at least part of said separated liquid back to the fermenter, the flow rate at which said separated liquid is recycled into said fermenter being from 1 to 10 times the flow rate at which said sugar-containing liquid that is fed into said fermenter; and discharging a residue from the fermentation system.

2. A process according to claim 1 wherein said sugar-containing liquid has a sugar concentration of 250 to 400 g/l.

3. A process according to claim 1 wherein said immobilized microorganism is immobilized on and inside the carrier and said carrier is at least one member selected from the group consisting of agar, alginate, Kappa-carrageenan, gelatin, collagen, polyacrylamide and photocrosslinked resins.

4. A process according to claim 1 wherein said alcohol fermentation is effected under a pressure ranging from 0 to 2 Kg/cm²G.

5. A process according to claim 1 wherein said alcohol-containing vapor contains 20 to 60 wt.% of ethanol.

6. A process according to claim 1 wherein said separated liquid in the flash tank is cooled to a temperature of 20° to 35° C. and is recycled to the fermenter.

7. A process according to claim 1 in which said flash tank is maintained under said reduced pressure by an ejector.

8. A process according to claim 1 wherein in the fermentation system, a number n of fermenters are arranged in series, the sugar-containing liquid is continuously supplied to the first fermenter from the outside of the system, the fermentation liquid taken out of said first fermenter is then heated and introduced into a first flash tank for dividing it into a first alcohol-containing vapor and a first separated liquid; the first separated liquid is cooled and part of it is recycled to the first fermenter and the balance is introduced into the second fermenter; the fermentation liquid taken out of the second fermenter is then heated and introduced into a second flash tank for separating it into a second alcohol-containing vapor and a second separated liquid; the second separated liquid is cooled and part of it is recycled to the second fermenter; the same procedure being repeated in the same manner for each fermenter, except for the final fermenter in the series, so that a liquid separated in a given flash tank is cooled and part of it is recycled to the fermenter associated with said given flash tank and the balance is introduced into the next following fermenter to provide the fermentation liquid for the next following fermenter, and wherein in each heating step the portion of the fermentation liquid that is removed from the preceding fermenter is heated to 50° to 80° C., and each flash tank is held under a reduced pressure of 60 to 300 mg Hg absolute.

9. A process according to claim 8 wherein n is a number from 2 to 5.

10. A process according to claim 8 wherein said sugar-containing feed liquid has a sugar concentration of 250 to 400 g/l.

11. A process according to claim 8 wherein said immobilized microorganism is immobilized on and inside the carrier and said carrier is at least one member selected from the group consisting of agar, alginate, Kappa-carrageenan, gelatin, collagen, polyacrylamide and photocrosslinked resins.

12. A process according to claim 8 wherein said alcohol fermentation is effected under a pressure ranging from 0 to 2 Kg/cm$^2$G.

13. A process according to claim 8 wherein said alcohol-containing vapor contains 20 to 60 wt.% of ethanol.

14. A process according to claim 8 wherein said separated liquid in the flash tank is cooled to a temperature of 20° to 35° C. and is recycled to the fermenter.

15. A process according to claim 8 in which said flash tank is maintained under said reduced pressure by an ejector.

16. A continuous alcohol manufacturing process which comprises: continuously mixing together a fermentable sugar-containing, feed liquid and a fermentable recycle liquid to form a fermentation liquid and feeding said fermentation liquid into a fermenter that is packed with an alcohol-producing microorganism which is immobilized on a solid carrier; fermenting said fermentation liquid in said fermenter at a temperature of from 25° to 35° C. and at a pressure of from 0 to 2 Kg/cm$^2$G to produce alcohol; continuously removing from the fermenter a stream consisting of a portion of the fermentation liquid, heating said stream to a temperature of from 50° to 80° C. and then feeding said heated stream into a flash tank which is maintained at a reduced pressure of from 60 to 300 mm Hg absolute whereby to form in said flask tank an alcohol-containing vapor and said recycle liquid; removing said vapor from said flash tank and then condensing said vapor to obtain an alcohol-containing liquid; recovering said alcohol-containing liquid; removing said recycle liquid from said flash tank, cooling at least part of said recycle liquid to a temperature of from 20° to 35° C. and then feeding it into said fermenter as said fermentable recycle liquid, the flow rate at which said recycle liquid is recycled into said fermenter being from 1 to 10 times the flow rate at which said fermentable feed liquid is fed into said fermenter; and discharging a residue from the process.

17. A process according to claim 16 wherein said sugar-containing feed liquid has a sugar concentration of 250 to 400 g/l.

18. A process according to claim 16 wherein said immobilized microorganism is immobilized on and inside the carrier and said carrier is at least one member selected from the group consisting of agar, alginate, Kappa-carrageenan, gelatin, collagen, polyacrylamide and photocrosslinked resins.

19. A process according to claim 16 wherein said alcohol-containing vapor contains 20 to 60 wt.% of ethanol.

20. A process according to claim 16 in which said flash tank is maintained under said reduced pressure by an ejector.

21. A continuous alcohol manufacturing process, which comprises: continuously mixing together a fermentable, sugar-containing, feed liquid and a first fermentable recycle liquid to form a first fermentation liquid and feeding said first fermentation liquid into a first fermenter that is packed with an alcohol-producing microorganism which is immobilized on a solid carrier; fermenting said fermentation liquid in said first fermenter to produce alcohol; continuously removing from said first fermenter a first stream consisting of a portion of the first fermentation liquid, heating said first stream to a temperature of from 50° to 80° C. and then feeding said heated first stream into a first flash tank which is maintained at a reduced pressure of from 60 to 300 mm Hg absolute whereby to form in said first flash tank a first alcohol-containing vapor and a first separated liquid; removing said first vapor from said flash tank and then condensing said first vapor to obtain a first alcohol-containing liquid; removing said first separated liquid from said first flash tank, cooling part of said first separated liquid to a temperature of from 20° to 35° C. and then continuously feeding it into said first fermenter as said first fermentable recycle liquid, the flow rate of said first recycle liquid that is recycled into said first fermenter being from 1 to 10 times the flow rate of said fermentable feed liquid that is fed into said first fermenter; continuously mixing the balance of said first separated liquid and a second fermentable recycle liquid to form a second fermentation liquid and feeding said second fermentation liquid into a second fermenter that is packed with an alcohol-producing microorganism which is immobilized on a solid carrier; fermenting said second fermentation liquid in said second fermenter to produce alcohol; continuously removing from said second fermenter a second stream consisting of a portion of the second fermentation liquid, heating said second stream to a temperature of from 50° to 80° C. and then feeding said heated second stream into a second flash tank which is maintained at a reduced pressure of from 60 to 300 mm Hg absolute whereby to form in said second flash tank a second alcohol-containing vapor and a second separated liquid; removing said second vapor from said second flash tank and then condensing said second vapor to obtain a second alcohol-containing liquid; removing said second separated liquid from said second flash tank, cooling part of said second separated liquid to a temperature of from 20° to 35° C. and then feeding it into said second fermenter as said second fermentable recycle liquid, the flow rate of said second recycle liquid that is recycled into said second fermenter being from 1 to 10 times the flow rate of the balance of said first separated liquid that is fed into said second fermenter; and removing said first and second alcohol-containing liquids for recovery and discharging a residue of said second separated liquid.

22. A process according to claim 21 wherein said sugar-containing feed liquid has a sugar concentration of 250 to 400 g/l.

23. A process according to claim 21 wherein said immobilized microorganism is immobilized on and inside the carrier and said carrier is at least one member selected from the group consisting of agar, alginate, Kappa-carrageenan, gelatin, collagen, polyacrylamide and photocrosslinked resins.

24. A process according to claim 21 wherein said alcohol fermentation is effected under a pressure ranging from 0 to 2 Kg/cm$^2$G.

25. A process according to claim 21 wherein said alcohol-containing vapor contains 20 to 60 wt.% of ethanol.

26. A process according to claim 21 in which first and second flash tanks are maintained under said reduced pressure by an ejector.

* * * * *

UNITED STATES PATENT AND TRADEMARK OFFICE
CERTIFICATE OF CORRECTION

PATENT NO. : 4 680 263

DATED : July 14, 1987

INVENTOR(S) : Tomiaki YAMADA et al

It is certified that error appears in the above-identified patent and that said Letters Patent is hereby corrected as shown below:

Column 9, line 48; delete "that".

Column 10, line 57; change "mg" to ---mm---.

Column 12, line 61; after "which" insert ---said---.

Signed and Sealed this

Fifth Day of January, 1988

Attest:

DONALD J. QUIGG

Attesting Officer

Commissioner of Patents and Trademarks